United States Patent [19]

Kankare et al.

[11] Patent Number: 4,920,195
[45] Date of Patent: Apr. 24, 1990

[54] FLUORESCENT LANTHANIDE CHELATES

[76] Inventors: Jouko Kankare, Paljaspää 8E3, SF-206 10 Turku 61; Harri Takalo, Ursininkatu 13A4, SF-20100 Turku 10; Paavo Pasanen, Menninkaisenkatu 10E37, SF-20640 Ravattula, all of Finland

[21] Appl. No.: 149,980

[22] Filed: Jan. 25, 1988

Related U.S. Application Data

[63] Continuation-in-part of Ser. No. 863,047, May 14, 1986, abandoned.

[30] Foreign Application Priority Data

May 23, 1985 [SE] Sweden ............................ 8502573

[51] Int. Cl.$^5$ .................. C07F 5/00; G01N 33/533; C07D 213/38; C07D 213/55
[52] U.S. Cl. .................................. 534/16; 534/15; 436/546; 546/1; 546/2; 546/5
[58] Field of Search ......................... 534/15, 16

[56] References Cited

U.S. PATENT DOCUMENTS

| | | | |
|---|---|---|---|
| 3,928,509 | 12/1975 | Diery et al. ...................... | 260/945 |
| 3,957,863 | 5/1976 | Diery et al. ...................... | 260/534 |
| 3,974,090 | 8/1976 | Mitchell ........................ | 260/502.4 P |
| 3,994,966 | 11/1976 | Sundberg et al. ............... | 260/518 R |
| 4,058,732 | 11/1977 | Wieder ........................... | 250/461 |
| 4,133,873 | 1/1979 | Noller ............................ | 436/518 |
| 4,144,224 | 3/1979 | Moser ............................ | 260/45.75 |
| 4,228,184 | 10/1980 | Ondetti et al. ................. | 562/443 |
| 4,259,313 | 3/1981 | Frank ............................ | 424/1.1 X |
| 4,293,466 | 10/1981 | Di Battista et al. ............. | 260/45.8 |
| 4,341,957 | 7/1982 | Wieder ........................... | 250/461 |
| 4,353,751 | 10/1982 | Baudouin et al. ............... | 106/306 |
| 4,355,034 | 10/1982 | Shen et al. ..................... | 546/334 |
| 4,374,120 | 2/1983 | Soini ............................. | 436/546 |
| 4,565,790 | 1/1986 | Hemmila et al. ................. | 436/537 |
| 4,637,988 | 1/1987 | Hinshaw et al. ................. | 436/546 |
| 4,639,365 | 1/1987 | Sherry ............................ | 534/16 X |
| 4,761,481 | 8/1988 | Hale et al. ..................... | 534/16 X |
| 4,772,563 | 9/1988 | Evangelista et al. ............. | 534/16 X |
| 4,801,722 | 1/1989 | Hinshaw et al. ................. | 534/16 X |
| 4,810,782 | 3/1989 | Theodoropulos .................. | 534/15 |
| 4,837,169 | 6/1989 | Toner ............................ | 436/546 |

FOREIGN PATENT DOCUMENTS

| | | | |
|---|---|---|---|
| 82/86330 | 7/1982 | Australia ........................ | 562/443 |
| 1028347 | 3/1978 | Canada ........................... | 260/501.5 |
| 0064484 | 11/1982 | European Pat. Off. . | |
| 0068875 | 1/1983 | European Pat. Off. . | |
| 0133310 | 2/1985 | European Pat. Off. . | |
| 2537275 | 2/1977 | Fed. Rep. of Germany . | |
| 53-23924 | 6/1978 | Japan ............................ | 562/443 |
| 723316 | 2/1955 | United Kingdom ............... | 562/443 |
| 1363099 | 8/1974 | United Kingdom ............... | 562/443 |
| 1598610 | 9/1981 | United Kingdom ............... | 562/443 |

OTHER PUBLICATIONS

Chemical Abstracts, 92:110799z, (1980).
Chemical Abstracts, 92:22173/r, (1980).
Smith et al., Ann. Clin. Biochem., 18, (1981), 253–274.
Ullman, Edwin F., "Ligand Assay, Recent Advances in Fluorescence Immunoassay Techniques", (1981), pp. 113–135.
Soini et al., Chin. Chem., 25, (1979), 353–361.
Hnatowich et al., Int. J. Appln. Radiat. Isot., 33, (1982), pp. 327–332.
Klopper et al., J. Nucl. Med., 13, (1972), pp. 107–110.
Leung, Biochem. & Biophys. Res. Comm., vol. 75, No. 1, 1977, pp. 149–155.
Wieder, Chem. Abs., vol. 90, 1979, (citing Immounoflouresc. Tech. Proc. Int. Conf. 6th, 1978, p. 67080).
Makhijani et al., J. Ind. Chem. Soc., vol. 60, 1978, pp. 840–841.
Nakatani et al., Rev. Phys. Chem., Japan, vol. 42, 1972, pp. 103–107.
Moller et al., Chem. Rev., vol. 65, 1965, pp. 1, 10, 13 and 25 to 50.
Halverson, (1964), J. Chem. Phys., 41, 157.
Taketatsu, (1979), Anal. Chim. Acta, 108, 429.
Brittain, (1980), Inorg. Chem. 19, 640.

Primary Examiner—Brooks H. Hunt
Assistant Examiner—Virginia B. Caress
Attorney, Agent, or Firm—Fisher, Christen & Sabol

[57] ABSTRACT

A fluorescing lanthanide chelate of a lanthanide cation and a compound having the structure (Abstract continued on next page.)

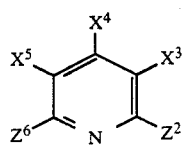

where $X^3$, $X^4$ and $X^5$ that may be the same or different, each denotes a substituted ethynyl group, hydrogen, an alkyl group, an aryl group, a hydroxyl group, an alkoxyl group or an amino group, wherein at least one of $X^3$, $X^4$ and $X^5$ denotes a substituted ethynyl group, and $Z^2$ and $Z^6$ that may be the same or different, each denotes a chelating group, hydrogen, an alkyl group or an amino group, wherein at least one of $Z^2$ and $Z^6$ denotes a chelating group.

12 Claims, 1 Drawing Sheet

FLUORESCENT LANTHANIDE CHELATES

This is a continuation-in-part of application Ser. No. 863,047, filed May 14, 1986.

BACKGROUND OF THE INVENTION

1. Field of the Invention

This invention pertains to organic complexing agents capable of complexing with lanthanide cations and the formed lanthanide chelates useful as fluorescent compounds in the determination of physiologically active materials.

The sensitivity of the analytical methods based on molecular fluorescence is limited by the background signal due to either Roman scattering or fluorescent impurities in the sample. Both of these interferences are generally short-lived phenomena, i.e. the radiative transition following the excitation of the molecule occurs within a microsecond time span. Thus any compound with a long-lived fluorescence can be effectively determined in the presence of short-lived background if a fluorometer with time resolution is at hand. In this fluorometer the sample is illuminated by an intermittent light source such thay the long-lived fluorescence is measurable during the dark period subsequent to the decay of the short-lived background. This invention relates to the synthesis and use of such compounds with the long-lived fluorescence.

2. Description of the Prior Art

The long-lived fluorescence (0.1-3 ms lifetime) of certain chelates of rare-earth metals has been known for some time. The use of these chelates in fluorometric immunoassay (FIA) with time resolution has been described in German OLS 2,628,158 and U.S. Pat. No. 4,374,120. In these publications the complexing agents are aromatic diketones. In German OLS 2,628,158 the fluorescent chelate is "conjugated", i.e. convalently bound to the antigen or antibody. The main shortcoming in this work is the aqueous instability of the chelates which hinders the use of the method at low concentrations.

In Eur. Pat. Appl. 82850077.7 (publ. no. 64484) another ligand is attached either to the antigen or antibody. This ligand is non-fluorescent and serves only in carrying the lanthanide through the separation step of the antigen-antibody complex. After the separation the lanthanide cation is dissociated at low pH and another, fluorescent diketone chelate is formed and measured in aqueous micellar phase. This method gives a very good sensitivity but suffers from somewhat lengthy procedure.

It would be very advantageous to have fluorescent probes with good aqueous stability which would allow shorter assay procedures and also the use of probes in other methods than immunoassay, e.g. in fluorescence microscopy.

DESCRIPTION OF THE PREFERRED EMBODIMENTS

The compound according to the invention, which compound is to be used as a complexing agent, has the following structure:

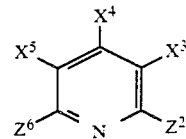

Each of $X^3$, $X^4$ and $X^5$ that may be the same or different, denotes a substituted ethynyl group, hydrogen, an alkyl group, an aryl group a hydroxyl group, an alkoxyl group or an amino group, but at least one of $X^3$, $X^4$ and $X^5$ denotes a substituted ethynyl group, and each of $Z^2$ and $Z^6$ that may be the same or different denotes a chelating group, hydrogen, an alkyl group, an aryl group, a hydroxyl group, an alkoxyl group or an amino group, but at least one of $Z^2$ and $Z^6$ denotes a chelating group. Fluorescing lanthanide chelates of such compounds can be used. The lanthanide used in such fluorescing lanthanide chelate is preferably terbium or europium.

In the compounds according to the invention, the restrictions are:

1. The carbon-carbon triple bond is conjugated with the pi-electron system of the pyridine ring. The selection of a triple bond instead of a single or double bond provides a rigidity to the molecule rendering it more difficult for absorbed energy to dissipate through rotational movement within the molecule.

2. The chelating groups are so selected and substituted on the pyridine ring that energy transfer from the chromophoric structure (conjugated pi-electron system) to a chelated lanthanide ion is favored. The pyridine nitrogen participates in the chelation.

3. $Z^2$ and $Z^6$ are both chelating groups. This gives quite an efficient protection against the transfer of absorbed energy to water molecules.

These three items are the heart of the invention. They define a group of compounds among which fluorescent lanthanide chelates can be found that very efficiently can be measured by time-delayed fluorescence spectrometry. Fluorescence can be measured even in aqueous media, a propety that has been rare for most known fluorescent lanthanide chelates. Compounds of the invention, accordingly, can be used as labelled reagents in favorable homogeneous immunoassays in which the time-resolved spectrofluorometric principle is employed.

The pyridine nitrogen participates in the chelating (is a donor atom).

The substituent in the ethynyl group may be either a substituted or unsubstituted aromatic group, e.g. a phenyl group or a naphthyl group, or a substituted or unsubstituted heteroaryl group, e.g. a pyridyl group, a quinolyl group, a thienyl group, a thiazolyl group, a benzthiazolyl group, a benzoxazolyl group or a benzimidazolyl group.

The chelating group is a heteroatom-containing group, e.g. a N,N-bis(carboxymethyl)aminomethyl group, a 2,6-dicarboxypiperidinomethyl group or a carboxyl group.

When both $Z^2$ and $Z^6$ denote the same heteroatom-containing groups, these groups may be joined by a bridge consisting of carbon and nitrogen atoms, so that the chelating group is a macrocycle. Preferred macrocyclic chelating compounds have the structure:

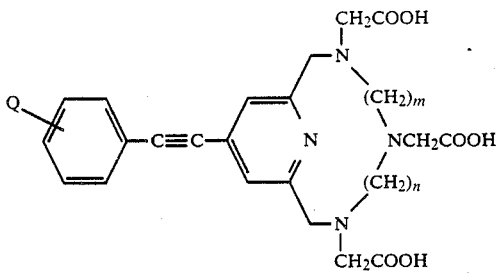

wherein n and m is 2 or 3 and Q is a group (such as amino or aminoalkyl) appended to the position 2′, 3′ or 4′ of the phenyl group used to link up the physiologically active material such as an immunoreagent.

In another preferred embodiment, the compound which complexes with the lanthanide metal has the following structure:

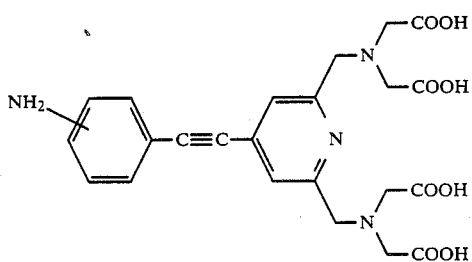

wherein the amino group may be appended to the positions 2′, 3′ or 4′ and the other positions of the phenyl ring may be substituted by alkyl, such as methyl or ethyl, hydroxyl, alkoxyl, such as methoxyl or ethoxyl, amino, or halogen, such as fluorine or chlorine groups.

A preferred fluorescently labeled binding reagent comprises a complex of a lanthanide metal having the structure:

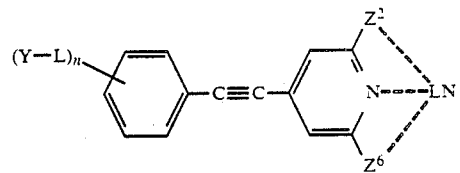

wherein L is a linking group, such as a ureido, thioureido, an amide, such as —CONH—, -CONMe—; thioether, such as —S—, —S—S—; sulfonamide, such as —SO$_2$NH—, —SO$_2$NMe—; n is 1 or 2, and Y is a physiologically active material. $Z^2$ and $Z^6$ have been described above.

The above compounds are also used as chelating ligands to replace the β-diketones described in the European Pat. Appln 82850077.7. In such cases the compounds would not have any linking groups.

Any fluorescent lanthanide metal can be used in the chelates, but the preferred lanthanide is europium.

EXAMPLE 1

Synthesis of 4-phenylethynyl-2,6-bis(N,N-bis(carboxymethyl)aminomethyl)pyridine

Figure 1:
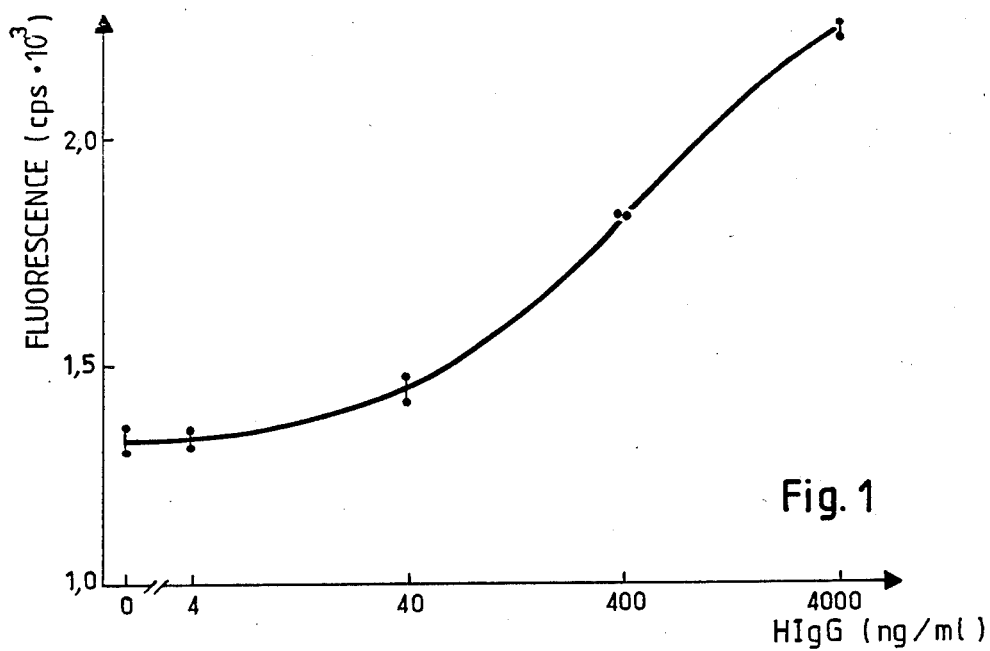
FIG. 1 of the accompanying drawings is a standard curve of fluorescence against added human IgG using a chelate of the present invention, as described in Example V below.

The synthetic scheme for the preparation of the title compound is as follows:

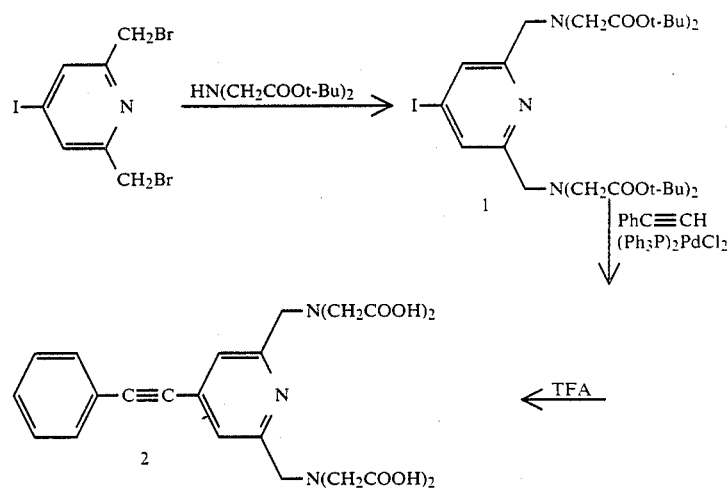

Preparation of 4iodo-2,6-bis(N,N-bis(t-butoxycarbonylmethyl)aminomethyl)pyridine (1)

To a solution of 4-iodo-2,6-bisbromomethylpyridine (0.59 g, 1.5 mmol) and di-t-butyl iminodiacetate (0.74 g, 3.0 mmol) in 40 mL of dry acetonitrile was added 1.59 g of sodium carbonate (15 mmol) and the mixture was stirred for 24 h at room temperature. Filtration and evaporation of the filtrate left a yellow oil. The oil was taken into 20 mL of chloroform, washed twice with 10 mL of water and dried with Na₂SO₄. Evaporation gave a yellowish oil which was purified by chromatographing on silica with toluene-ethanol (10:1).

Preparation of
4-phenylethynyl-2,6-bis(N,N-bis(carboxymethyl)aminomethyl)pyridine (2)

A mixture of compound 1 (0.63 g, 0.875 mmol), bis(triphenylphosphine)palladium(II) chloride (12 mg, 0.0175 mmol), copper(I) iodide (7 mg, 0.0368 mmol), and phenylacetylene (83 mg, 0.875 mmol) in 5 mL of triethylamine was deaerated with nitrogen and kept at 40° C. for 5 h. The mixture was diluted with 20 mL of chloroform and washed with water. The organic phase was dried with Na₂SO₄, filtered and evaporated. The resulting yellowish oil was characterized by nmr spectrum. Oil was dissolved in 20 mL of trifluoroacetic acid and kept at room temperature for 16 h. Trifluoroacetic acid was evaporated in vacuo, the solid residue was triturated with 15 mL of ethyl ether and finaly recrystallized from ethanol. The yield was 0.24 g (59%). $^1$H-NMR (DMSO): δ 3.20–3.60 (NH), 3.5 (8H), 3.98 (4H), 7.40–7.70 (7H), 12.30–12.60 (OH). IR (KBr): 2210 cm$^{-1}$ (C≡C), 1730, 1630, 1390, 1210 cm$^{-1}$ (C=O and C—O).

Fluorescence of the europium chelate of compound 2

The relative fluorescence yield $\Phi_{rel}$ of the europium chelate of compound 2 was measured in an equimolar $10^{-5}$M solution of compound 2 and europium chloride in pH 8.5 borate buffer. Fluorescence measurements were done on a Perkin-Elmer LS5 (trade mark) spectrofluorimeter using the phosphorescence mode which allowed the decay curves of the lanthanide fluorescence to be measured. The fluorescence yield is reported relative to the fluorescence of the uncomplexed europium cation using the equation:

$$\Phi_{rel} = \frac{I_{che}C_{Eu}k_{Eu}}{I_{Eu}C_{che}k_{che}}$$

where $I_{che}$ and $I_{Eu}$ are the preexponential terms of the emission decay curves measured at 615 nm for the chelated and uncomplexed europium, respectively. The excitation wavelength for the uncomplexed europium was 395 nm and for the chelate of compound 2 294 nm. $C_{Eu}$ and $C_{che}$ are the concentrations of free and complexed europium, respectively, and $k_{Eu}$ and $k_{che}$ the corresponding decay constants. For compound 2 the relative fluorescence yield becomes $7.8 \times 10^5$. This parameter is relatively independent on the instrument used for the measurement.

EXAMPLE II

Synthesis of 3,5-bis(phenylethynyl)-4-hydroxy-2,6-pyridinedicarboxylic acid (3)

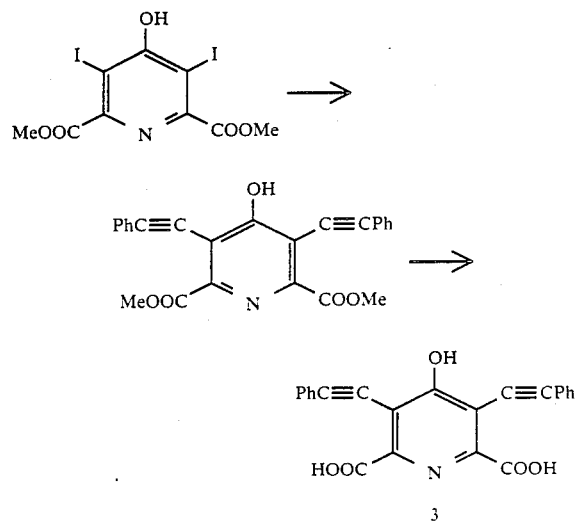

Dimethyl ester of 3,5-diiodo-4-hydroxy-2,6-pyridinedicarboxylic acid (1.0 g, 2.2 mmol), phenylacetylene (0.7 g, 6.9 mmol), palladium(II) acetate (19 mg, 0.085 mmol), triphenylphosphine (45 mg, 0.170 mmol) and copper(I) iodide (8 mg, 0.043 mmol) were dissolved in the mixture of triethylamine (15 mL) and dimethylformamide (5 mL). The mixture was stirred under nitrogen atmosphere for 24 h at room temperature and 7 h at 40° C.

Triethylammonium iodide was filtered off and filtrate evaporated in vacuo. The residue was dissolved in chloroform, washed with water, dried with sodium sulfate and evaporated. The residue was dissolved in the mixture of petroleum ether and ethyl acetate (10:7) and chromatographed on silica. The yield of the methyl ester of the title compound was 0.3 g (33%).

$^1$H-NMR (CDCl₃): 67 3.90 (6H), 7.80–7.15 (10H, arom.).

IR (KBr): 1735, 1210 cm$^{-1}$ (C=O and C—O), 2208 cm$^{-1}$ (C≡C).

Methyl ester was hydrolyzed by stirring at room temperature in 0.5M solution of KOH in ethanol for 4 h. The mixture was diluted with water and acidified to pH 1.5 with 6M hydrochloric acid. The mixture was stirred for 1 h, the precipitate filtered off and washed with water.

IR (KBr): 1720, 1330–1190 cm$^{-1}$ (C=O and C—O), 2206 cm$^{-1}$ (C≡C).

Relative fluorescence yield of the europium complex: $\Phi_{rel} = 1.4 \times 10^5$ at $\lambda_{ex}$ 330 nm.

EXAMPLE III

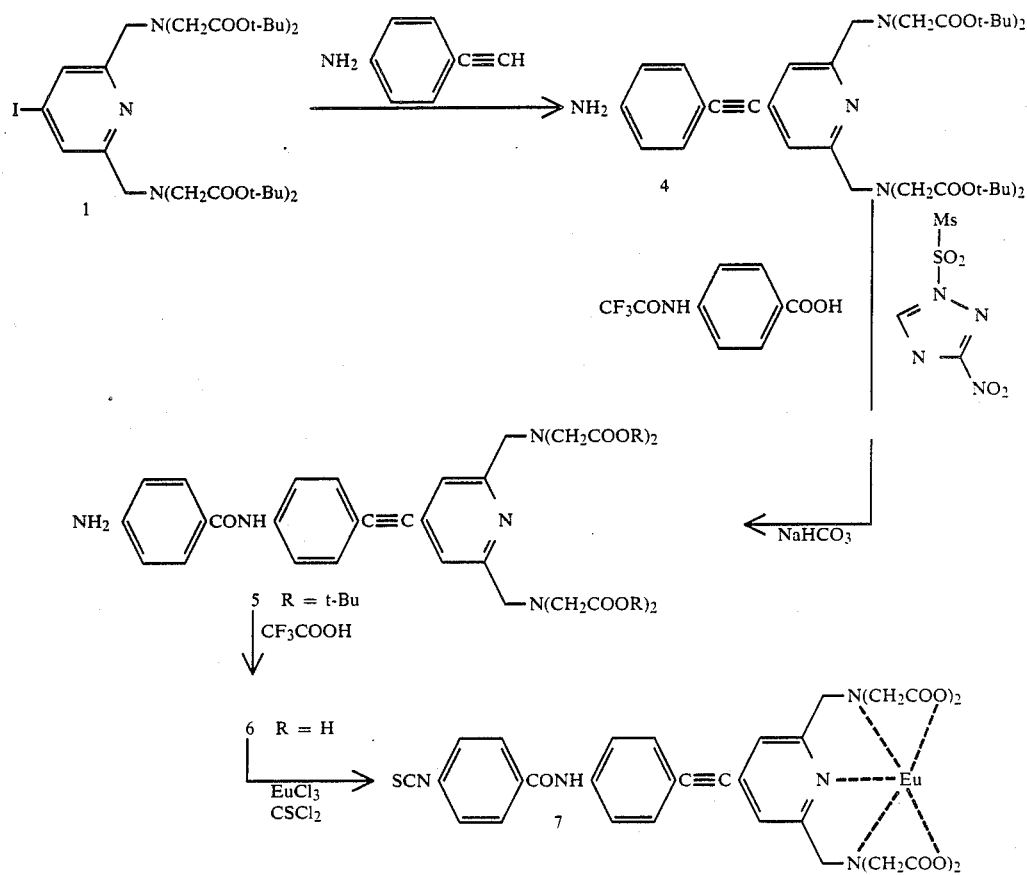

Preparation of 4-(4-aminophenylethynyl)-2,6-bis(N,N-bis(t-butoxycarbonylmethyl)aminomethyl)pyridine (4)

A mixture of compound 1 (1.08 g, 1.5 mmol), bis(triphenylphosphine)palladium(II) chloride (21 mg, 0.03 mmol), copper(I) iodide (11 mg, 0.06 mmol) and p-aminophenylacetylene (176 mg, 1.5 mmol) in 10 mL of triethylamine was deaerated with nitrogen and kept at 40° C. for 1.5 h. The mixture was diluted with 40 mL of chloroform, washed with water and dried with sodium sulfate. The solution was evaporated in vacuo and the product was obtained as a yellow oil.

$^1$H-NMR (CDCl$_3$): δ 1.47 (36H), 3.49 (8H), 4.02 (4H), 6.50–7.65 (6H). MS: parent peak at 708.

Preparation of 4-(4-(p-aminobenzamido)phenylethynyl)-2,6-bis(N,N-bis(t-butoxycarbonylmethyl)aminomethyl)pyridine (5) and the corresponding tetracarboxylic acid (6)

Compound 4 (60 mg, 0.084 mmol), 39 mg (0.168 mmol) of N-trifluoroacetyl-4-aminobenzoic acid and 2mL of dry pyridine were mixed and the solution was evaporated. The residue was dissolved in 1 mL of dry pyridine, and 200 mg (0.674 mmol) of 1-(2-mesitylenesulfonyl)-3-nitro-1,2,4-triazole was added. The solution was stirred for 45 min, 2 mL of concentrated sodium bicarbonate solution was added and the mixture was stirred for 10 min. The mixture was extracted with 5 mL of chloroform, the organic phase was separated and evaporated. The residue (compound 5) was purified with flash chromatography on a silica column with 5% of methanol in chloform as an eluent.

TLC (silica): R$_f$=0.33 in methanol-chloroform (1:9), R$_f$=0.78 in acetonitrile-water (4:1).

UV (ethanol): λ$_{max}$ 306 nm.

The product (compound 5) from the previous step (30 mg) was dissolved in 2.5 mL of trifluoroacetic acid and the solution was stirred overnight at room temperature. The solution was evaporated, the residue triturated with 5 mL of diethyl ether and the light yellow powder (compound 6) was filtered off.

TLC (silica): R$_f$=0.35 in acetonitrile-water (4:1).

UV (water, pH 9): λ$_{max}$298 nm.

Europium complex of compound 6 was prepared by dissolving 6 in water and adding equimolar amount of europium(III) chloride. The pH was adjusted to 8 and the solution was evaporated almost dry. A few milliliters of acetone was added and the product was filtered off. This compound was not further characterized but converted directly to the corresponding isothiocyanato compound for coupling purposes. The aforementioned europium complex (40 mg) was dissolved in 1 mL of water and 30 mg of sodium bicarbonate was added. Thiophosgene (25 μl) was dissolved in 1 mL of chloroform and this solution was added dropwise into the aqueous solution of europium chelate. The heterogeneous mixture was stirred for 1 h, some water and chloroform were added, and the phases were separated. The water phase was evaporated to almost dry, some acetone was added, and the precipitate (compound 7) was filtered off.

UV (water): λ$_{max}$ 333 nm.

EXAMPLE IV

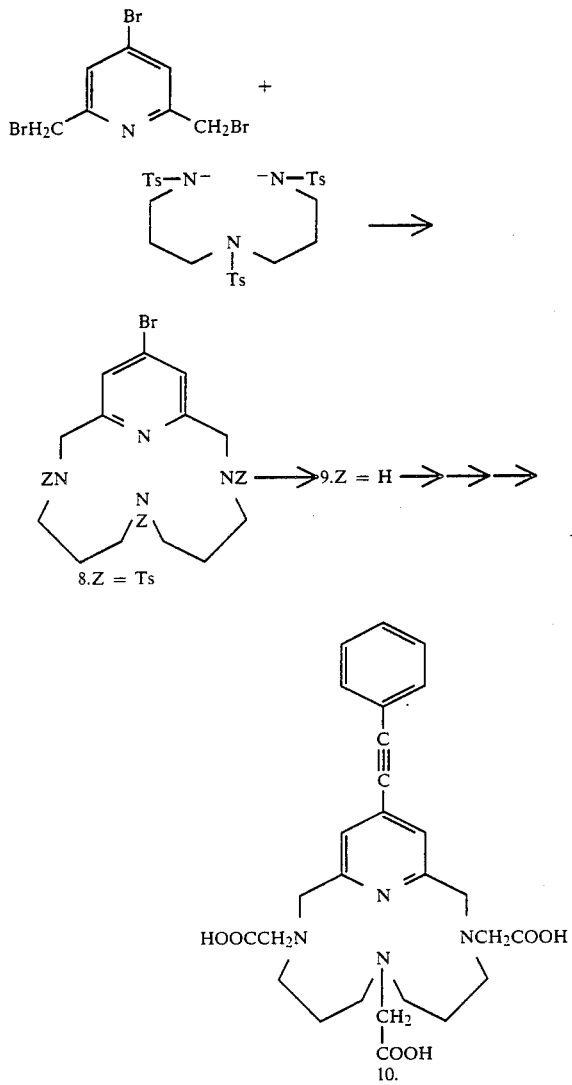

Synthesis of 15-bromo-3,7,11-tritosyl-3,7,11,17-tetraazabicyclo[11.3.1]-heptadeca-1(17),13,15-triene (8)

Disodium salt of N,N',N''-tritosyl-4-aza-1,7-heptanediamine (2.55 g, 4.0 mmol) was dissolved in 30 mL of DMF, and 1.37 g (4.0 mmol) of 4-bromo-2,6-bis-bromomethylpyridine in 25 mL of DMF was added at 75° C. during 1.5 h. The mixture was stirred at 75° C. for 2 h, 100 mL of water was added and the precipitate was filtered off and washed with water. After recrystallization from ethanol the yield of compound 8 was 2.66 g (86%), m.p. 187°–9° C.

$^1$H-NMR (CDCl$_3$): δ 1.62 (4H), 2.42 (3H), 2.45 (6H), 2.83 (4H), 3.24 (4H), 4.24 (4H), 7.29 (2H), 7.35 (4H), 7.59 (2H), 7.71 (2H), 7.72 (4H).

IR (KBr): 1595 cm$^{-1}$ (pyrid.), 1340, 1155 cm$^{-1}$ (SO$_2$).

Detosylation of compound 8

Compound 8 (2.65 g, 3.4 mmol) was dissolved in 18 mL of conc. sulfuric acid (95–98%) and stirred for 8 h at 105°–110° C. Sodium hydroxide solution (15%) was added to the cooled solution until its pH was ca. 10. The mixture was extracted with dichloromethane (8×60 mL). The extract was dried and evaporated on a rotary evaporator. The residue was yellow oil, which partly crystallized (0.65 g, 69%).

$^1$H-NMR (CDCl$_3$): δ 1.79 (4H), 2.66 (4H), 2.81 (4H), 3.26 (3H), 3.86 (4H), 7.33 (2H).

Synthesis of 15-phenylethynyl-3,7,11-tris(carboxymethyl)-3,7,11,17-tetraazabicyclo[11.3.1]heptadeca-1(17),13,15-triene (10)

Detosylated compound 8 (compound 9) (0.31 g, 1 mmol), 1.38 g (10 mmol) of potassium carbonate and 0.59 g (3 mmol) of t-butyl bromoacetate in 25 mL of dry acetonitrile was stirred for 24 h at room temperature. The mixture was filtered and the filtrate evaporated in vacuo. The resulting yellowish oil, bis(triphenylphosphine)palladium(II) chloride (14 mg, 0.02 mmol), copper(I) iodide (8 mg, 0.04 mmol) and phenylacetylene (102 mg, 1 mmol) were dissolved in the mixture of triethylamine (10 mL) and tetrahydrofuran (6 mL), the solution was deaerated with nitrogen and kept at 45° C. for 24 h. The mixture was filtered and the filtrate evaporated in vacuo. The resulting dark oil was dissolved in trifluoroacetic acid (20 mL) and kept at room temperature for 24 h. After evaporation the residue was triturated with ether, the solid residue was filtered off and washed with ether. The yield of white microcrystalline product was 0.6 g. IR (KBr): 2215 cm$^{-1}$(C≡C), 1730, 1680, 1200 cm$^{-1}$.

Relative fluorescence yield of the europium complex: $\Phi_{rel} = 1.6 \times 10^4$ at 80 $_{ex} = 294$ nm.

EXAMPLE V

Competitive assay of human IgG (HIgG) on solid phase by measuring the change of signal in solution Human IgG (1 mg) was labelled with the isothiocyanato derivative of Eu chelate (compound 7) by incubating it with 25-fold excess of the reagent in buffer solution (pH 9.5) at 4° C. overnight, and thereafter separating the unreacted fluorescent label from the conjugated HIgG by gel filtration on Sepharose 6B (Pharmacia Fine Chemicals).

10 ng of the labelled HIgG was then incubated in microtitration strip wells (Elfab, Finland) coated with rabbit-anti-human IgG together with HIgG standards (0–4000 ng/mL) in 0.25 mL of buffer containing BSA (DELFIA TM Assay Buffer, LKB-Wallac, Finland) at room temperature for 2 h, whereafter the fluorescence of solution in the strip wells was measured on a fluorometer with time resolution (1230 ARCUS, TM LKB-Wallac, Finland). The extent of binding of the labelled HIgG to the solid-phase bound antibodies was measured by reading the fluorescence intensity in solution. The labelled HIgG competes with the added standards. An increased standard concentration is seen as an increase in the measured signal as less of the labelled HIgG is bound to the rabbit-anti-human IgG on the solid phase (FIG. 1). The assay requires no actual separation as the result can be read from the incubation mixture.

EXAMPLE VI

Figure 2:
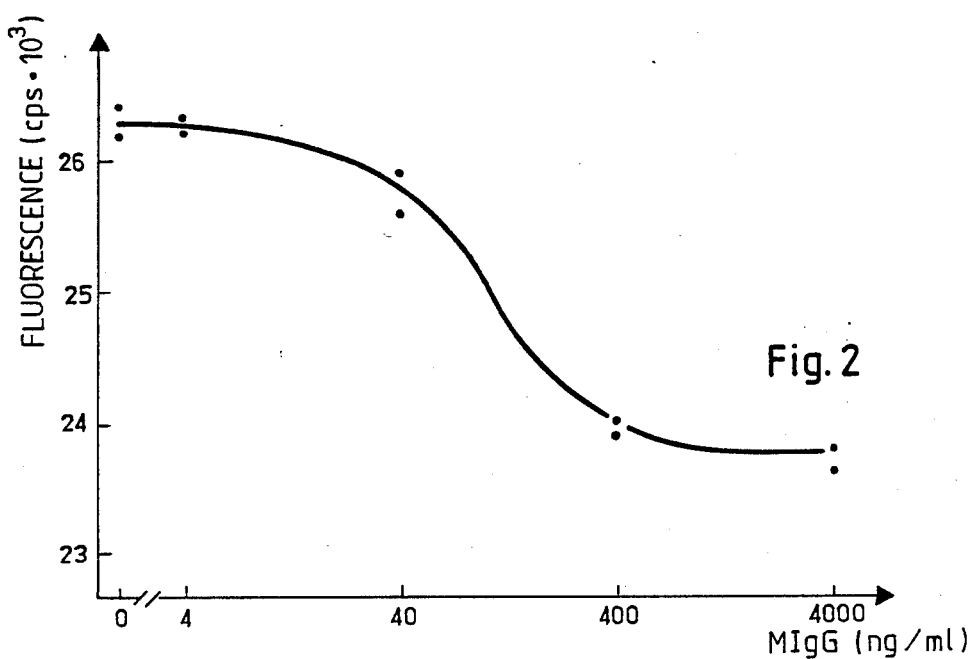
FIG. 2 is a standard curve similar to that of FIG. 1 but generated as described in Example VI below.

Sandwich fluorescence assay of mouse IgG (MIgG) by measuring the change of signal in solution Anti-mouse-IgG was labelled with the Eu-complex (7) as described in Example IV. A sandwich assay of mouse IgG was performed by incubating standards of MIgG (0–4000 ng/mL) in anti-mouse IgG coated strip wells for 2 h, whereafter (after washing) 200 ng/250 μL of the labelled anti-mouse-IgG in DELFIA ™ Assay buffer (LKB-Wallac) was added to the strips and incubated further 2 h at room temperature. After incubation the fluorescence of solution in the strip wells was measured on a fluorometer with time resolution. The resulting standard curve is presented in FIG. 2. As the MIgG concentration increases, more of the labelled anti-mouse-IgG is bound to the solid phase and the fluorescence signal in the incubation solution decreases.

We claim:

1. A fluorescing lanthanide chelate of a lanthanide cation and a compound having the structure:

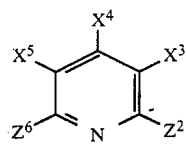

wherein each of $X^3$, $X^4$ and $X^5$, that can be the same or different, denotes a substituted ethynyl group directly attached to the pyridine ring, a hydrogen, an alkyl group, an aryl group, a hydroxyl group, an alkoxyl group or an amino group, wherein at least one of $X^3$, $X^4$ and $X^5$ denotes the substituted ethynyl group, and each of $Z^2$ and $Z^6$, that can be the same or different, denotes a chelating group that together with the pyridine nitrogen chelates the lanthanide cation.

2. Chelate according to claim 1 wherein the substituent in the ethynyl group is a substituted or unsubstituted aromatic group.

3. Chelate according to claim 2 wherein the aromatic group is a substituted or unsubstituted phenyl or pyridyl group.

4. Chelate according to claim 1 wherein the chelating group is a nitrogen- or oxygen-containing group.

5. Chelate according to claim 4 wherein the heteroatomcontaining group is a N,N-bis(carboxymethyl-)aminomethyl group, a carboxyl group or a 2,6-dicarboxypiperidinomethyl group.

6. Chelate according to claim 4 wherein $Z^2$ and $Z^6$ are joined by a bridge consisting of carbon and nitrogen atoms.

7. Chelate according to claim 2 wherein the lanthanide is terbium or europoim.

8. Chelate according to claim 1 wherein said compound has the structure:

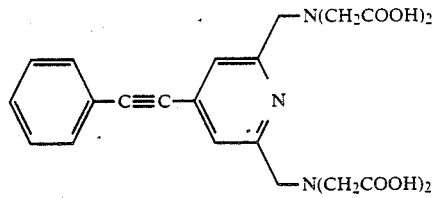

9. Chelate according to claim 1 wherein said compound has the structure:

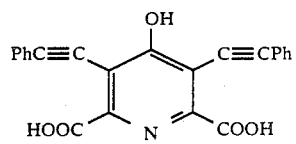

10. Chelate according to claim 1 wherein said compound has the structure:

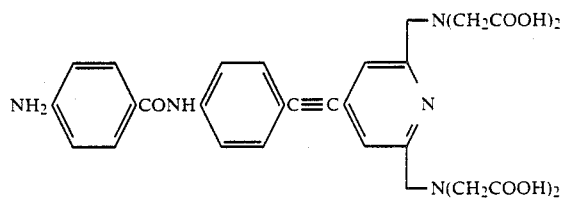

11. Chelate according to claim 1 having the structure:

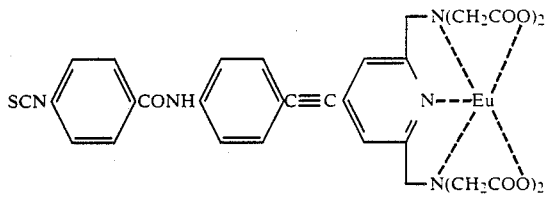

12. Chelate according to claim 1 wherein said compound has the structure:

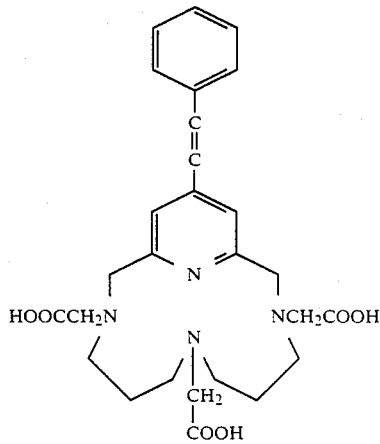

* * * * *